United States Patent [19]
Pritchard et al.

[11] Patent Number: 5,101,832
[45] Date of Patent: Apr. 7, 1992

[54] METHOD AND APPARATUS FOR MAKING ELECTRICAL MEASUREMENTS IN THE PRESENCE OF PERIODIC ELECTROMAGNETIC FIELDS

[75] Inventors: Bruce A. Pritchard; Daniel J. Powers, both of McMinnville; Jim T. Belesiu, Portland, all of Oreg.

[73] Assignee: Hewlett-Packard Company, Palo Alto, Calif.

[21] Appl. No.: 652,958

[22] Filed: Feb. 8, 1991

[51] Int. Cl.$^5$ ............................................. A61B 5/0428
[52] U.S. Cl. .................................... 128/696; 128/901; 324/99 D
[58] Field of Search ............... 128/696, 702, 706, 708, 128/901; 364/413.05, 413.06; 324/99 D

[56] References Cited
U.S. PATENT DOCUMENTS

| | | | |
|---|---|---|---|
| 3,354,453 | 11/1967 | Hibbits et al. | 324/99 D |
| 3,480,949 | 11/1969 | Charbonnier | 324/99 D |
| 4,243,045 | 1/1981 | Maas | 128/696 |
| 5,010,887 | 4/1991 | Thornander | 128/696 |

Primary Examiner—William E. Kamm
Assistant Examiner—Jeffrey R. Jastrzab

[57] ABSTRACT

A cardiograph has a remote front end which is connected to a host via a cable. The front end includes a clock and an analog-to-digital converter. The converter periodically holds and samples patient ECG signals. Each conversion takes place within the same fixed length of time. A clock signal is transmitted to the host on one of the conductors in the cable while digital words, each of which represents a sampled value of the ECG signal, are serially transmitted on another conductor in the cable. The clock signal synchronizes ac voltages applied to several power supplies with the sampling rate of the converter so that the ECG signal is sampled at the same phase of each ac voltage applied to the power supplies. The sampling thus occurs at the same phase, and thus the same amplitude, of each periodic noise cycle induced by the power supply electromagnetic fields. The periodic noise is thus removed from the sampled signal while a dc offset equal to the amplitude of the periodic noise at the sampling phase is added.

23 Claims, 3 Drawing Sheets

METHOD AND APPARATUS FOR MAKING ELECTRICAL MEASUREMENTS IN THE PRESENCE OF PERIODIC ELECTROMAGNETIC FIELDS

BACKGROUND OF THE INVENTION

1. Field of the Invention

The present invention relates to methods and apparatus for making electrical measurements in the presence of periodic electromagnetic fields and more particularly to such methods and apparatus which enable electrical measurement of a low amplitude signal of interest in the presence of a high energy oscillator.

2. Description of the Related Art

Accurate measurement of low amplitude signals of interest in the presence of an oscillating electromagnetic field poses a problem. The oscillating field imposes periodic noise on the conductor(s) carrying the signal thus producing inaccurate measurements. This is especially so in the case where a signal of interest is periodically sampled, held and then converted to a digital value because sampling may occur at different phases of the periodic noise signal. Even if the sampling rate is synchronized with the periodic noise signal, variations in the length of time for the digital conversion to occur permit random noise levels to appear on the held signal.

One instrument in which such problems arise is a cardiograph. A cardiograph includes a plurality of leadwires which are connected to a patient's skin via electrodes for sensing electrical signals generated by the patient's heart. Such signals are low amplitude and have a bandwidth of roughly 0.5 to 150 hertz. A cardiograph includes one or more power supplies which each incorporate a transformer or inductor to which an oscillating voltage signal is applied. The power supplies generate periodic electromagnetic fields which are induced on the leadwires and other conductors carrying the signals of interest from the patient.

In one prior art cardiograph, an analog signal of interest is sampled, and thereafter held, at a rate which is an integer multiple of the power supply frequency. In the prior art conversion process, the signal is sampled and held in an isolated portion of the cardiograph. The held signal is pulse width modulated, i.e., a pulse having a width proportional to the magnitude of the held signal is generated. A synchronizing signal is taken from the secondary of an isolation transformer which provides power to the isolated circuit. Responsive to the synchronizing signal, a digital word representing the pulse width is generated and transmitted via an isolation coupling to a nonisolated portion of the cardiograph.

This prior art system suffers from a disadvantage in that the time during which the analog signal is converted depends upon the magnitude of the held signal. Because the duration of the conversion process is variable, and not necessarily in phase with the periodic noise, inaccuracies are injected into the conversion process.

In another prior art analog-to-digital conversion process implemented in a cardiograph, the dc offset is subtracted from an analog signal and the resulting signal is amplified. The amplified signal is sampled and held with the held signal being provided to an analog-to-digital converter of the dual-slope integration type. The signals which initiate each conversion process are synchronized to the power supply. Each conversion process is thus initiated at the same phase of the power supply signal as is the case with the pulse-width-modulated system described above. This prior art system is complex in that preconditioning of the analog signal, including subtracting the dc offset, is required.

In an effort to minimize the effects of periodic noise induced by power supplies, prior art cardiographs utilize expensive and bulky shielding around power supplies to limit radiation of the oscillating field. Prior art cardiographs also use filtering schemes to minimize noise in the signals of interest. Such filtering may reduce noise but it has the disadvantage of modifying information contained in the signals of interest.

SUMMARY OF THE INVENTION

The present invention comprises a method for making electrical measurements in the presence of a periodic electromagnetic field. The waveform of interest is sampled and the sampling rate is synchronized with the period of the electromagnetic field. Each sampled value is converted to a digital value in a fixed time interval.

Because the signal induced by the electromagnetic field is periodic and because sampling and conversion of each sample occur upon each reoccurrence of substantially the same phase of the induced periodic noise signal, the effect is one of a constant dc offset imposed on the waveform of interest.

In another aspect of the invention, a synchronizing signal is derived from a clock signal generated in an isolated portion of the cardiograph. The synchronizing signal is provided to an analog-to-digital converter in the isolated portion for sampling a waveform of interest. The synchronizing signal is also communicated via an isolation coupling to a nonisolated portion for synchronizing the isolated and nonisolated power supplies.

Apparatus is provided for implementing the method.

It is a general object of the present invention to provide a method and apparatus for making electrical measurements in the presence of periodic electromagnetic fields which overcome the above-enumerated disadvantages associated with prior art methods and apparatus.

It is a more specific object of the present invention to provide such a method and apparatus which does not require bulky and expensive shielding or filtering for reducing noise induced by the electromagnetic field.

It is another object of the present invention to provide a method and apparatus which is implemented in a cardiograph.

The foregoing and other objects, features and advantages of the invention will become more readily apparent from the following detailed description of a preferred embodiment which proceeds with reference to the drawings.

DETAILED DESCRIPTION OF THE PREFERRED EMBODIMENT

Figure 1A:
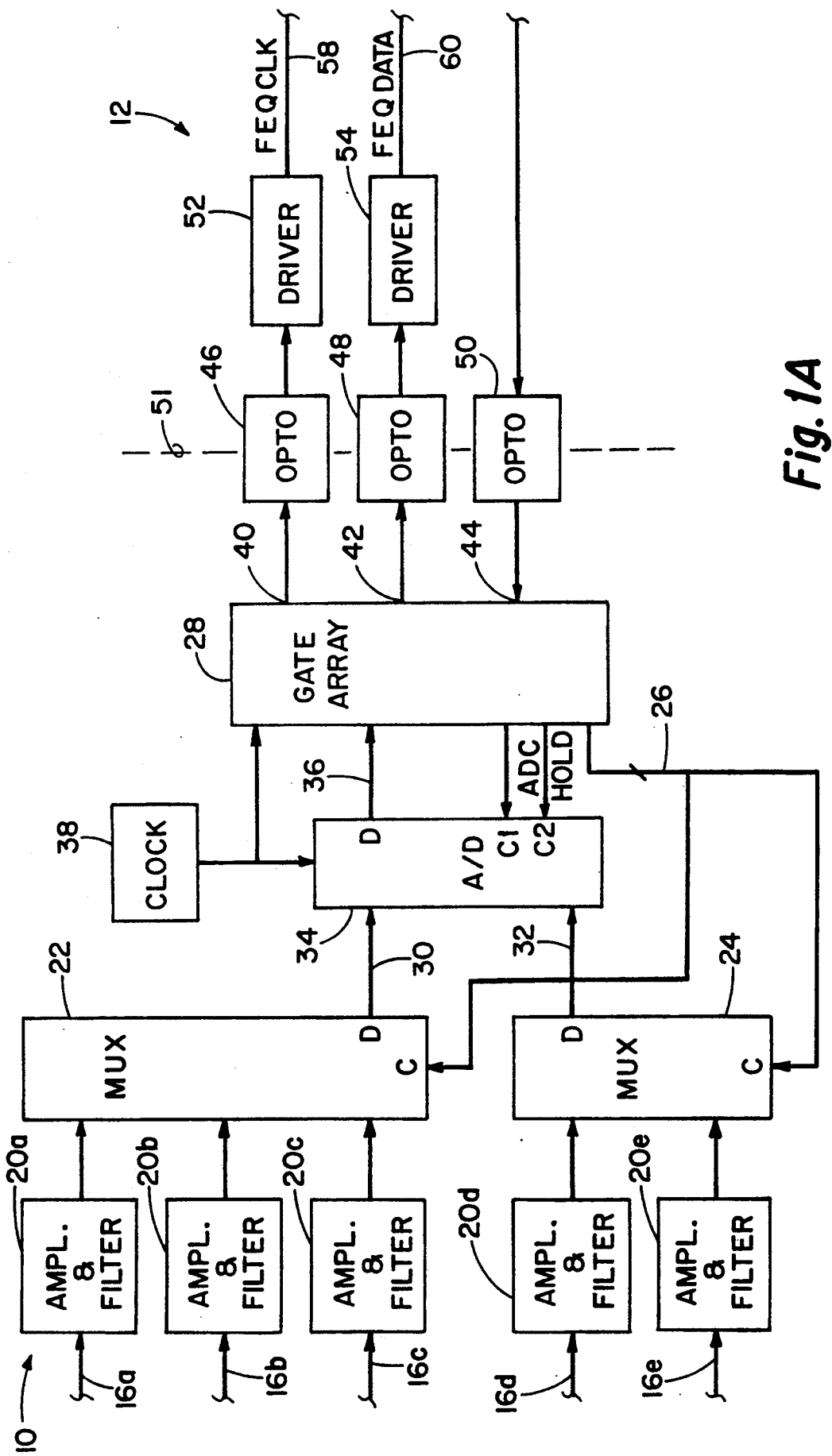
FIGS. 1A and 1B are a partial block diagram of a cardiograph constructed in accordance with the present invention.
Figure 1B:
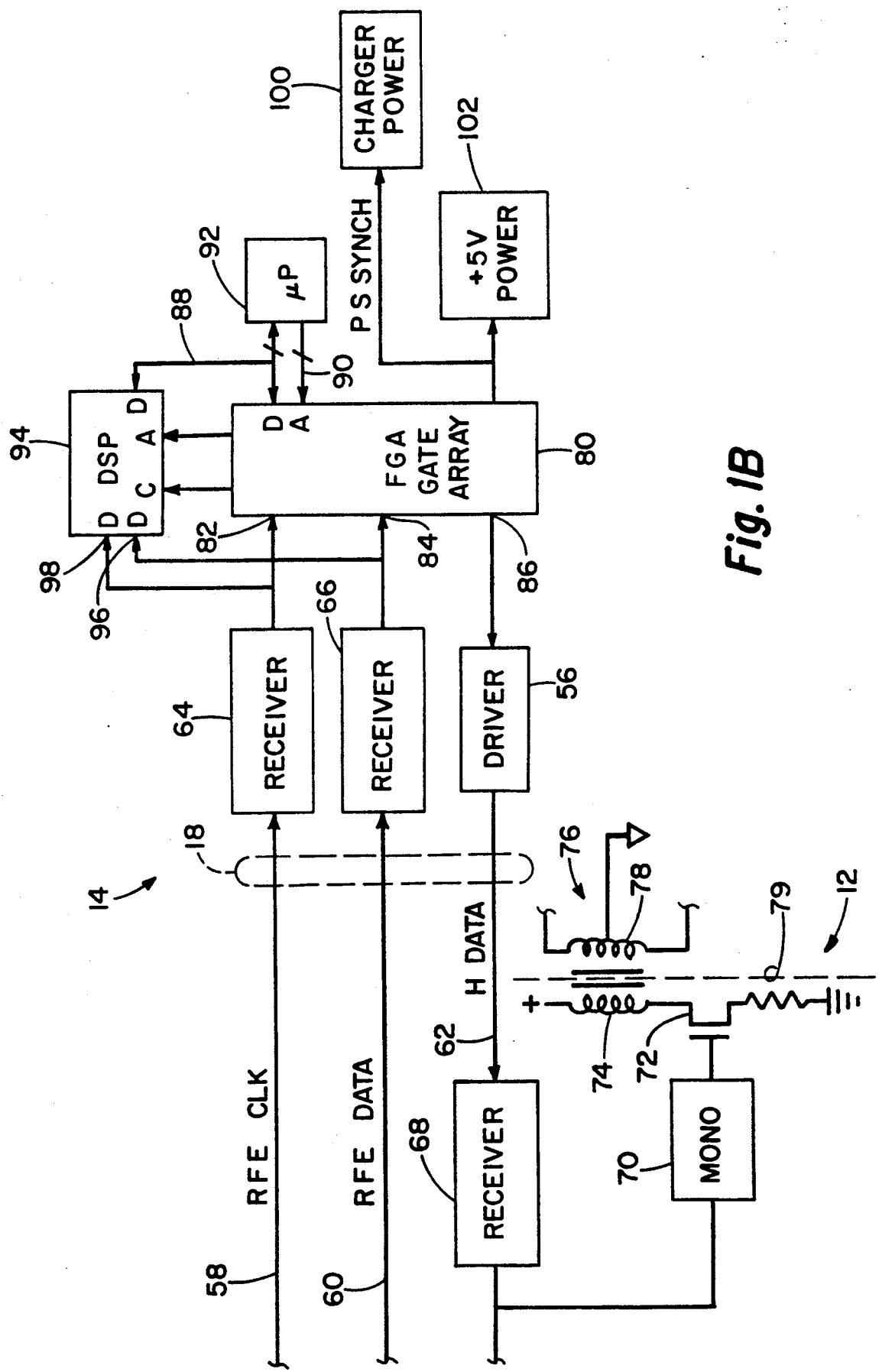

Turning now to FIGS. 1A and 1B, indicated generally at 10 is a partial block diagram of a cardiograph constructed in accordance with the present invention.

The components of cardiograph 10 are included within a remote front end (abbreviated herein as RFE), indicated generally at 12, and a host indicated generally at 14 in FIG. 1B. Front end 12 and host 14 are connected by a multi-conductor cable 18 (in FIG. 1B). The front end is about the size of two slices of bread stacked together while the host is approximately the size of a personal computer.

The remote front end includes a plurality of leadwires, five of which are leadwires 16a, 16b, 16c, 16d, 16e, which are connected to the skin of a person (not shown) for sensing signals generated by the person's heart and conducting them to front end 12.

Generally speaking, remote front end 12 is placed on or closely adjacent the patient and the leadwires, like leadwires 16a–e, are connected via electrodes to the patient's skin in a known manner. Through various pushbuttons (not shown) in remote unit 12 and host 14, an operator can cause cardiograph 10 to sense, store and display patient signals on the leadwires.

Considering now in more detail the structure of front end 12, each of exemplary leadwires 16a–e is connected to the input of an amplifier and associated filter circuits, 20a–e, respectively, to amplify and condition signals on the leadwire. The output of each of circuits 20a–c is connected to a different input of a conventional multiplexer 22. Similarly, the outputs of circuits 20d, 20e are connected to the inputs of a conventional multiplexer 24.

Multiplexer 22 operates in the usual fashion. Different ones of the signals appearing on the input of multiplexers 22 are serially selected, responsive to the data on control bus input C, to appear on output terminal D of the multiplexer. Multiplexer 24 operates in the same fashion.

Control lines 26 provides control signals from a gate array 28 to each of the control terminals on multiplexers 22, 24. A pair of data lines 30, 32 connect data terminal D on each of multiplexers 22, 24, respectively, to different input terminals of an analog-to-digital converter 34. In the present embodiment of the invention, converter 34 is manufactured by Crystal Semiconductor Corporation and identified as Model CS5101. This converter utilizes successive approximation for converting analog signals to digital signals and thus makes each conversion in the same fixed time. In the present embodiment of the invention, the conversion takes place in substantially less than a single power supply period.

Generally speaking, converter 34 includes a pair of input terminals to which data lines 30, 32 are respectively connected. Converter 34 includes a pair of control terminals C1, C2 which receive control signals from gate array 28. Control terminal C1 is operatively connected to a multiplexer internal to converter 34. A high signal on terminal C1 selects one of the converter input terminals while a low signal selects the other for conversion of the analog signal thereon to digital form. A transition from high to low on control terminal C2 holds the analog value on the input terminal selected by the signal on control terminal C1 and causes converter 34 to digitize the held value. The digitized value is serially applied by converter 34 to a data input of gate array 28 via line 36.

A clock 38 provides a periodic 6.256 megahertz clock signal to clock inputs of both converter 34 and gate array 28. Clock 38 is an integral part of converter 34.

Gate array 28 is an application specific integrated circuit (ASIC) which manipulates data supplied thereto and generates control signals in a manner which will be described in more detail hereinafter. Given a set of input signals and the desired output signals, which are described hereinafter and shown in FIG. 2, a person having ordinary skill in the art could design a gate array to produce such signals.

Gate array 28 includes serial output terminals 40, 42 and a serial data input terminal 44. Each of terminals 40, 42, 44 is connected to an optoisolator 46, 48, 50. The optoisolators isolate patient-connected circuitry in front end 12 from the rest of the cardiograph for safety reasons. That portion of cardiograph 10 to the left of dashed line 51 in FIG. 1A is referred to herein as an isolated portion of the cardiograph. The optoisolators isolate signals by converting a signal on the input of each optoisolator to a light signal which is converted back to a voltage signal with the input and output of each optoisolator thus being electrically isolated.

Figure 2:
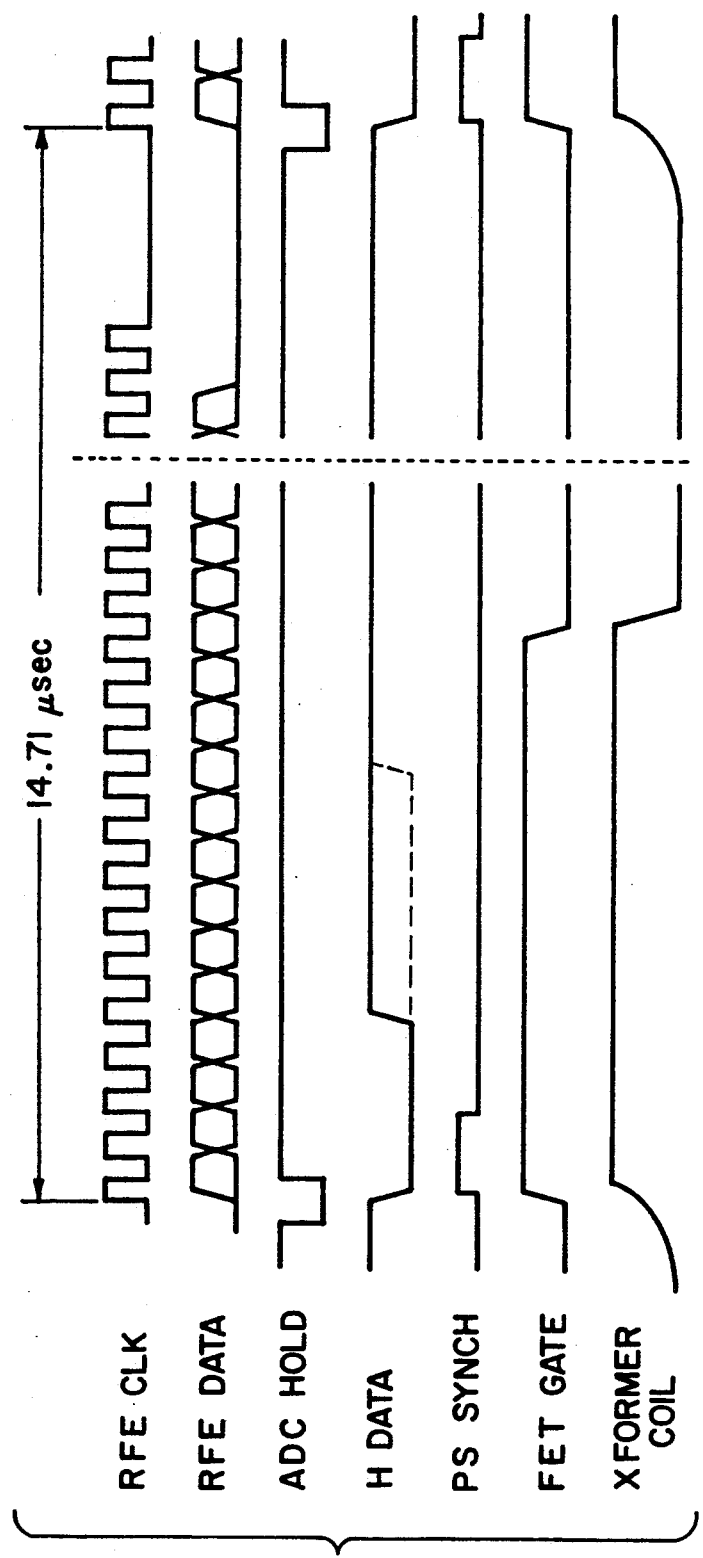
FIG. 2 is a timing diagram of selected voltage signals generated by the cardiograph of FIGS. 1A and 1B.

Line drivers 52, 54, 56 amplify the signals applied thereto with the amplified output of each driver being connected to conductors 58, 60, 62, respectively. The drivers prevent unacceptable attenuation of the signals in cable 18. Each such amplified signal is detected by a receiver 64, 66, 68 after transmission through cable 18. As can be seen, conductors 58, 60 provide signals from front end 12 to host 14 while conductor 62 provides a signal from the host to the front end. Each of conductors 58, 60, 62 includes a signal name, RFE CLK (remote front end clock), RFE DATA (remote front end data) and H DATA (host data), respectively, which identifies the signal on each conductor. These signals are illustrated in FIG. 2 and are discussed further hereinafter.

The signal on conductor 62, in addition to being provided to gate array input terminal 44 via receiver 68 and optoisolator 50, is also provided (via receiver 68) to the input of a conventional monostable multivibrator 70. Conventional filtering and conditioning circuitry (not shown) process the signal prior to the input of multivibrator 70. A pulse applied to the input of multivibrator 70 is converted to a pulse of constant duration on the output thereof.

The multivibrator output drives a FET 72 which is connected to a primary coil 74 of an isolation power-supply transformer, indicated generally at 76. That portion to the right of dashed line 79 is in the isolated portion of remote front end 12. A secondary coil 78 is on the isolated side of the remote front end and thus provides power to the electrically isolated portion of remote front end 12.

An 11 volt dc power supply voltage is applied to a conductor (not shown) in cable 18 at host 14 to provide the dc voltage which is applied to the top side of primary coil 74 in the remote front end. The ac voltage appearing on secondary coil 78 is applied to a rectifier (not shown) and filtered in the usual fashion to provide dc power supply voltages for the components contained in the isolated portion (to the left of dashed line 51 in FIG. 1A) of front end 12. The power supply in the front end is thus electrically isolated from host 14.

Considering now structure included in host 14, a gate array 80 is an ASIC which generates control signals and manipulates data supplied thereto in a manner which is described in more detail hereinafter in connection with the description of the operation of the cardiograph and with reference to the signals generated in FIG. 2. Given the signals and data supplied thereto, and the desired output signals and data signals, a person having ordinary skill in the art could design a gate array, like gate array 80, to provide the desired functions.

Gate array 80 includes a pair of serial data input terminals 82, 84 and a serial data output terminal 86. These terminals are operatively connected to conductors in cable 18 as previously described. Gate array 80 is connected to a data bus 88 and an address bus 90 which are connected to the usual data and address terminals of a conventional microprocessor 92. Data bus 88 is also connected to the data terminals of a conventional digital signal processor 94.

In the present embodiment of the invention, the digital signal processor is manufactured by Motorola and sold under the Model No. DSP56001. Processor 94 includes a pair of serial data input terminals 96, 98 which are connected to the outputs of receivers 64, 66. A control terminal C on processor 94 receives a signal generated by gate array 80 for synchronizing clocking data into terminals 96, 98 of DSP 94. An address decoding terminal A causes data to be clocked from the DSP on bus 88 responsive to digital control signals applied to terminal A of gate array 80.

Another control signal generated by gate array 80, PSSYNCH, is applied to a battery charger power supply circuit 100 and to a 5 volt dc power supply 102. PSSYNCH synchronizes the power supply for a battery charger (not shown) which maintains batteries (also not shown) in a charged condition so that the cardiograph may be operated with voltage supplied by the batteries, if necessary. Power supply 102 provides a conventional power supply for various components in host 14 of the cardiograph. As described further hereinafter, each power supply 100, 102 is synchronized by PS SYNCH in the same fashion that H DATA synchronizes the isolated supply powered by transformer 76.

In operation, signals on leadwires 16a–e are amplified and conditioned by circuits 20a–e, respectively. Each amplified and conditioned signal is applied to a different input of one of multiplexers 22, 24 as shown in FIG. 1A. A digital control signal (not shown) generated by gate array 28 is applied to control lines 26. A different one of lines 26 applies a different control signal to each control terminal C of multiplexers 22, 24. The control signal applied to control terminal C of multiplexer 22 sequentially and periodically selects a different one of the inputs and applies the same to the multiplexer output terminal and therefore to data line 30. The control signal applied to control terminal C of multiplexer 24 effects the same sequential and periodic action in multiplexer 24.

As previously mentioned, clock 8 provides a 6.256 megahertz digital clock signal to both converter 34 and gate array 28. Among other things, gate array 28 produces what is referred to herein as a periodic sample control signal, ADC HOLD in FIG. 2, and applies the same to control terminal C2 of converter 34. A converter and multiplexer control signal (not shown in FIG. 2) is also generated by gate array 28 and applied to control terminal C1 of multiplexer 34 which, as will be recalled, chooses a different one of the analog signals appearing on data lines 30, 32 for digitizing responsive to a high to low transition on control terminal C2. The digital control signals generated by gate array 28 and applied to control terminal C1 periodically and alternately chooses the signals on lines 30, 32 for holding a selected value in time and digitizing the value. Concurrently therewith the previously digitized value is passed to gate array 28 on data line 36. As can be seen by examining ADC HOLD in FIG. 2, a held value of one of the analog signals applied to lines 30, 32 is digitized every 14.71 microseconds. In the next 14.71 microsecond period, the signal appearing on the other of lines 30, 32 is held and digitized in the same fashion.

RFE CLK, in FIG. 2, is generated by gate array 28 and applied to terminal 40. Each 14.71 microsecond period of RFE CLK includes 26 2.085 megahertz frequency pulses followed by a 2.47 microsecond time during which the signal is gated low. RFE CLK is used to synchronize both the host-to-remote front end and the remote front end-to-host communications channels described hereinafter.

RFE DATA is also generated by gate array 28 and applied to terminal 42 thereof. Each 14.71 microsecond period of RFE DATA includes a 24-bit word followed by a time, during which RFE DATA is gated low, which identifies the start of the next word. Each word includes a single sampled value, in a 16-bit digital number, which is provided to the gate array on line 36. Each bit in RFE DATA is valid on the falling edge of RFE CLK.

The sequence for digitizing analog signals on lines 30, 32 and transmitting the digitized information on conductor 60 in cable 18 to host 14 is as follows: each high to low transition of ADC HOLD on control terminal C2 of converter 34 digitizes the instantaneous value of one of the analog signals on lines 30, 32 thereby creating a 16-bit number N+2. At the same time, the previous digitized value, 16-bit number N+1, is transferred from converter 34 to gate array 28 on line 36. Also at the same time, gate array 28 transmits 16-bit number N, packed in a single 24-bit word of RFE DATA, to the host via terminal 42 of the gate array.

Every 17 words of RFE DATA, with each word comprising a 14.71 microsecond period as shown in FIG. 2, comprise a frame. Sixteen of the words each includes a 16-bit number, representing the sampled value of a patient signal, packed into the 24-bits with the seventeenth word comprising one word of miscellaneous data such as error detection information, a datum to indicate whether or not a pushbutton (not shown) in the remote front end is depressed, a reset handshake bit and a framing bit. The framing bit is the twenty-fourth bit and is set to a high level for the word containing miscellaneous data and to a logic zero for each of the other 16 words, thus signalling the beginning and ending of each frame.

Each falling edge of RFE CLK on terminal 98 of DSP 94 latches a data bit on terminal 96 of the DSP. RFE DATA is thus clocked into the DSP which can be caused to filter the digital data. After processing by the DSP, the data is made available to the microprocessor on data bus 88. When microprocessor 92 is ready to receive data from DSP 94 on bus 88, the microprocessor provides a DSP address on bus 90 to gate array 80. The gate array generates a digital address decoded signal and applies the same to terminal A of the DSP which causes data to be clocked from the DSP to microprocessor 92 on bus 88.

The RFE DATA signal is provided to gate array 80 on terminal 84 to permit circuitry in host 14 to determine whether or not conductor 60 in the cable is broken in a manner which is known in the art. Each of the other conductors in the cable are monitored in a similar fashion.

RFE CLK is provided to gate array 80 on terminal 82 for several purposes. First, gate array 80 synchronizes, via a signal applied to terminal C of DSP 94 and derived from RFE CLK, clocking of data in RFE DATA into digital signal processor 94. Secondly, PS SYNCH, in FIG. 2, is derived from RFE CLK and applied to power supplies 100, 102 to synchronize the power supplies with the start of each 14.71 microsecond period in a manner which is described more fully hereinafter. Finally, RFE CLK is also used by gate array 80 to time an H DATA signal, in FIG. 2, which is applied to terminal 86 of gate array 80.

FIG. 2 illustrates a portion of an H DATA signal in its normal operating mode. Normal operation occurs when power is on and front end 12 is connected to host 14 via cable 18. In this mode, H DATA provides a power supply synchronization pulse once in each 14.71 microsecond period. This pulse always begins with the first RFE CLK pulse after the period in which RFE CLK is gated low.

Each H DATA pulse is either 4 RFE CLK pulses in width, as illustrated by the solid-line depiction of H DATA in FIG. 2, or is a total of 10 RFE CLK pulses in width, as illustrated by the solid and dashed-line depiction. The wide H DATA pulse represents a data "1" or a start-bit, signifying the start of a data word, while the narrow pulse represents a data "0". From time to time host 14, under control of microprocessor 92, sends data to remote front end 12 via the H DATA signal. Such data is always initiated with a start-bit, which is a wide H DATA pulse, followed by 11 data bits, with the most significant first and a parity bit at the end. When data is not being transmitted, H DATA comprises a series of narrow pulses synchronized with RFE CLK as depicted in FIG. 2. Again, the falling edge of each H DATA pulse, regardless of whether data is being transmitted or not, starts with the rising edge of the first RFE CLK pulse after a period in which RFE CLK is gated low.

H DATA controls such functions as turning the remote front end power supply on and off, cable continuity testing, message writing to a liquid crystal display (not shown) on the remote front end, initializing the display, calibrating converter 34, etc.

As can be seen with reference to FIGS. 1A, 1B and 2, each H DATA pulse triggers multivibrator 70 to produce a pulse on the gate of FET 72 which is designated FET GATE in FIG. 2. Such a pulse drives transformer 76 to produce an ac voltage in the secondary designated XFORMER COIL in FIG. 2. The ac voltage, and the consequent electromagnetic field produced by transformer 76, is thus synchronized with each of the other signals illustrated in FIG. 2.

In a similar fashion to H DATA, PS SYNCH, in FIG. 2, is a periodic pulse which is initiated at the beginning of each RFE CLK pulse train after the period in which the RFE CLK is gated low. PSSYNCH is provided to power supplies 100, 102 and thus synchronizes them in the same manner that the supply powered by transformer 76 is synchronized.

Figure 3:
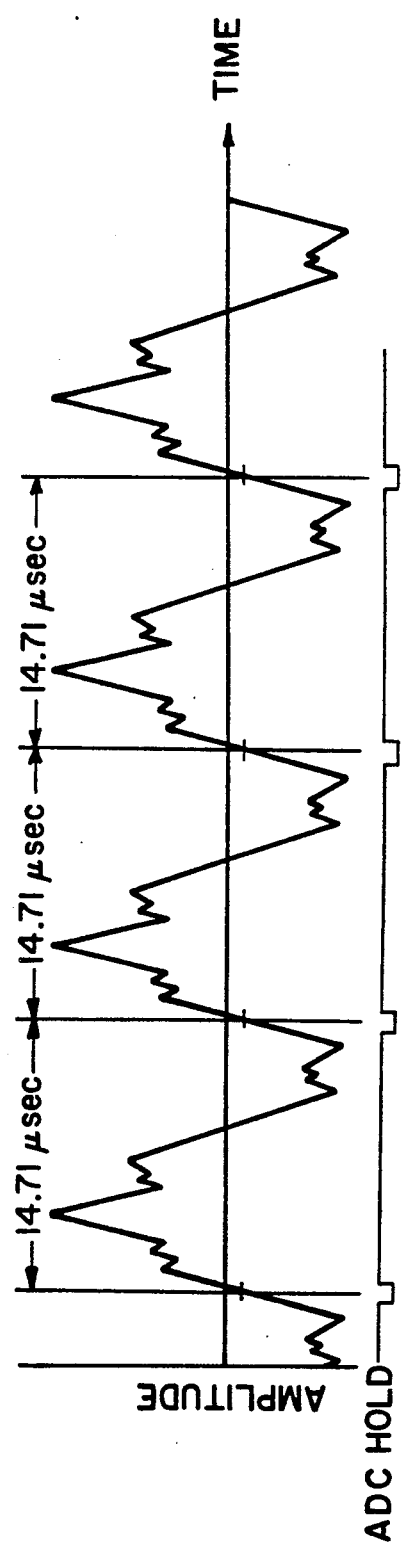
FIG. 3 is a plot of a periodic electromagnetic field generated in the power supply circuits of the cardiograph of FIGS. 1A and 1B.

Turning now to FIG. 3, illustrated therein is a plot of the amplitude of a periodic electromagnetic field which is generated by transformer 76 as well as by power supplies 100, 102. Because the transformers and inductors are synchronously driven, responsive to the H DATA and PS SYNCH pulses as described above, the periodic electromagnetic field generated by each power supply in cardiograph 10 is in phase with the fields generated by the other power supplies.

The ADC HOLD signal is also in phase with the emf field as illustrated in FIG. 3. Thus, the analog signals generated by the patient are sampled at the downward-going edge of each ADC HOLD pulse and therefore occur at the same phase, and thus substantially the same amplitude, of each cycle of the electromagnetic field. Because the electromagnetic field induces a proportional voltage into leadwires and other conductors which carry the analog signal of interest, and because the conversion process occurs within a fixed time interval, the effect of sampling as illustrated in FIG. 3 is to impose a constant dc bias onto the signal of interest and to remove noise injected by the periodic electromagnetic field. In the present embodiment of the invention, a software-implemented filter is used to remove the dc offset imposed on the digitized signals.

If, however, absolute signal magnitude is of interest, the transformer drive voltage could be briefly removed while the signal of interest is sampled thereby removing the dc offset imposed as described above.

It is to be appreciated that the present invention can be implemented when signal measurement is required.

As used herein, the terms "cardiograph" refer to any system for sensing patient electrical signals and processing such signals for storage and/or display.

Having illustrated and described the principles of our invention in a preferred embodiment thereof, it should be readily apparent to those skilled in the art that the invention can be modified in arrangement and detail without departing from such principles. We claim all modifications coming within the spirit and scope of the accompanying claims.

We claim:

1. A method for making electrical measurements in the presence of a periodic electromagnetic field comprising the steps of:
    generating a periodic power supply voltage with a predetermined period;
    periodically sampling a waveform of interest at a predetermined sampling rate;
    holding each sampled value;
    converting each sampled value to a digital value;
    limiting the time for converting each sampled value to the same predetermined period; and
    synchronizing the sampling rate with the period of the power supply voltage.

2. The method of claim 1 wherein the step of synchronizing the sampling rate with the period of said power supply voltage comprises the step of sampling the waveform upon each reoccurrence of substantially the same phase of said power supply voltage.

3. The method of claim 2 wherein the step of generating a periodic power supply voltage comprises the step of:
    generating a clock signal;
    generating a periodic power-supply drive signal derived from the clock signal and synchronous therewith; and
    using the power-supply drive signal to generate a periodic signal which produces the periodic power supply voltage.

4. The method of claim 3 wherein said method further includes the steps of:
   generating a periodic sample control signal derived from the clock signal and having the same period as said power-supply drive signal; and
   sampling the waveform of interest responsive to each occurrence of the sample control signal.

5. The method of claim 4 wherein:
   the power-supply drive signal is generated in a nonisolated portion of a cardiograph; and
   the periodic power supply voltage, the clock signal and the sample control signal are generated in an isolated portion of the cardiograph.

6. The method of claim 5 wherein said method further includes the step of coupling the clock signal from the isolated to the nonisolated portion of the cardiograph.

7. The method of claim 6 wherein said cardiograph includes an isolation power supply, which generates the periodic power supply voltage, and a nonisolated power supply and wherein said method further includes the step of using the coupled clock signal to synchronize the nonisolated power supply with the rate at which the waveform of interest is sampled.

8. Apparatus for making electrical measurements in the presence of a periodic electromagnetic field comprising:
   means for generating a periodic power supply voltage with a predetermined period;
   means for sampling a waveform of interest at a predetermined sampling rate;
   means for converting each sampled value to a digital value within the same predetermined period; and
   means for synchronizing the sampling rate with the period of such a power supply voltage.

9. The apparatus of claim 8, wherein said power supply voltage has a phase angle said means for synchronizing the sampling rate with the period of said power supply voltage comprises means for sampling the waveform upon each reoccurrence of substantially the same phase angle of said power supply voltage.

10. The apparatus of claim 9 wherein said means for generating a periodic power supply voltage comprises:
    means for generating a clock signal;
    means for generating a periodic power-supply drive signal derived from the clock signal and synchronous therewith; and
    a load operatively connected to such a power-supply drive signal, said load generating the periodic power supply voltage when driven by such a drive signal.

11. The apparatus of claim 10 wherein said apparatus further includes:
    means for generating a periodic sample control signal derived from the clock signal and having the same period as the drive signal; and
    means for sampling the waveform of interest responsive to each occurrence of the sample control signal.

12. The apparatus of claim 11 wherein:
    said means for generating a power supply drive signal and said means for generating a periodic power supply voltage are received in a nonisolated portion of a cardiograph; and
    said means for generating a clock signal and said means for generating a periodic sample control signal are received in an isolated portion of the cardiograph.

13. The apparatus of claim 12 wherein said apparatus further includes means for coupling the clock signal from the isolated to the nonisolated portion of the cardiograph.

14. The apparatus of claim 13 wherein said cardiograph includes a first power supply received in said isolated portion and a second power supply received in said nonisolated portion and wherein said apparatus further includes means for synchronizing the nonisolated power supply with the rate at which the waveform of interest is sampled, said synchronizing means being responsive to said coupled clock signal.

15. A method of obtaining cardiographic data from a patient comprising the steps of:
    affixing leadwires to the patient's body;
    detecting signals on the leadwires;
    sampling each signal at a periodic sampling rate frequency;
    holding each sampled signal;
    converting each held signal to a digital value within a fixed time interval;
    generating an ac voltage having a periodic frequency for powering circuits used in connection with obtaining the cardiographic data; and
    synchronizing the ac voltage and the sampling rate.

16. The method of claim 15 the ac voltage has a phase angle wherein the step of synchronizing the ac voltage and the sampling rate comprises the step of sampling the signal upon each reoccurrence of substantially the same phase angle of said ac voltage.

17. The method of claim 16 wherein said method further includes the steps of:
    generating a clock signal;
    generating a periodic drive signal derived from the clock signal and synchronous therewith;
    using the drive signal to generate the ac voltage;
    generating a periodic sample control signal derived from the clock signal and synchronous therewith; and
    sampling the signal responsive to each occurrence of the sample control signal.

18. The method of claim 17 wherein said method further includes the step of encoding said periodic drive signal with data.

19. Apparatus for obtaining cardiographic data from a patient comprising:
    leadwires affixable to a patient's body;
    means for detecting a signal on each leadwire;
    means for periodically sampling the detected signal at a predetermined sampling rate;
    a power supply including means for generating an ac voltage having a periodic frequency;
    means for synchronizing the ac voltage and the sampling rate;
    an electrically isolated portion which includes said detecting means and said sampling means and to which each leadwire is connectable;
    means for generating a clock signal received in said isolated portion; and
    means for communicating said clock signal from said isolated portion to said synchronizing means.

20. The apparatus of claim 19 wherein said apparatus further includes:
    means for generating a periodic sample control signal derived from the clock signal and synchronous therewith; and
    means for generating a periodic drive signal derived from the clock signal and synchronous therewith, said means for generating a periodic drive signal being operatively connected to said means for generating an ac voltage.

21. The apparatus of claim 20 wherein said apparatus further includes means for encoding said periodic drive signal with data.

22. The apparatus of claim 21 wherein said data includes information for controlling circuits in said apparatus.

23. The apparatus of claim 21 wherein said apparatus further includes:
an electrically nonisolated portion which includes said means for generating a periodic drive signal; and
means for coupling said clock signal from said isolated portion to said nonisolated portion.

* * * * *